United States Patent [19]
Nichols et al.

[11] Patent Number: 5,099,005
[45] Date of Patent: Mar. 24, 1992

[54] METHOD OF ENHANCING IMMUNOGLOBULIN FRAGMENT PRODUCTION

[75] Inventors: Everett J. Nichols, Edmonds; Robert F. McIntyre, Seattle, both of Wash.

[73] Assignee: NeoRx Corporation, Seattle, Wash.

[21] Appl. No.: 589,984

[22] Filed: Sep. 28, 1990

[51] Int. Cl.⁵ .............................................. C07K 3/08
[52] U.S. Cl. .................... 530/388.1; 435/68.1; 530/387.1; 530/866; 530/409
[58] Field of Search ............... 435/68.1; 530/388, 389, 530/409, 390, 391

[56] References Cited

U.S. PATENT DOCUMENTS

| | | | |
|---|---|---|---|
| 4,397,183 | 8/1983 | Ultee et al. | 530/388 |
| 4,814,433 | 3/1989 | Fredrickson | 530/388 |
| 4,859,449 | 8/1989 | Mattes | 530/389 |

OTHER PUBLICATIONS

Gilbert Ashwell and A. G. Morrell: The Role of Surface Carbohydrates in the Hepatic Recognition of Circulating Glycoproteins, in Advances in Enzymology, vol. 41, pp. 99-128.

Primary Examiner—Jeffrey E. Russel
Assistant Examiner—P. L. Touzeau
Attorney, Agent, or Firm—Stoel Rives Boley Jones & Grey

[57] ABSTRACT

Methods of enhancing immunoglobulin fragment yield of immunoglobulins exhibiting anomalous bands when analyzed by SDS-PAGE techniques are provided. Such yield enhancement methods include the steps of desialylating the immunoglobulin; and fragmenting the immunoglobulin produced in the desialylating step. A particular advantage of the present invention is that the fragmention step can be carried out in the presence of cysteine without decreasing the quality of the immunoglobulin fragment product. Methods of enhancing the molecular weight homogeneity of immunoglobulin or fragmented immunoglobulin exhibiting anomalous bands when analyzed by SDS-PAGE techniques are also discussed. These methods include the steps of desialylating the immunoglobulin or fragmented immunoglobulin and purifying the desialylated product.

8 Claims, 6 Drawing Sheets

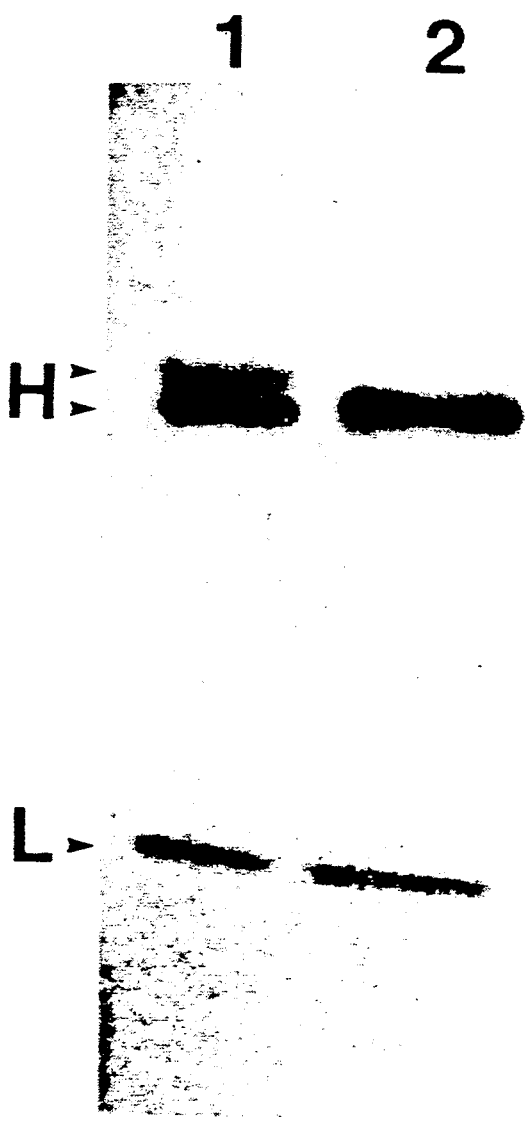

0.1M  0.5M

FT  0.1M  0.5M

FIG. 5A
FIG. 5B
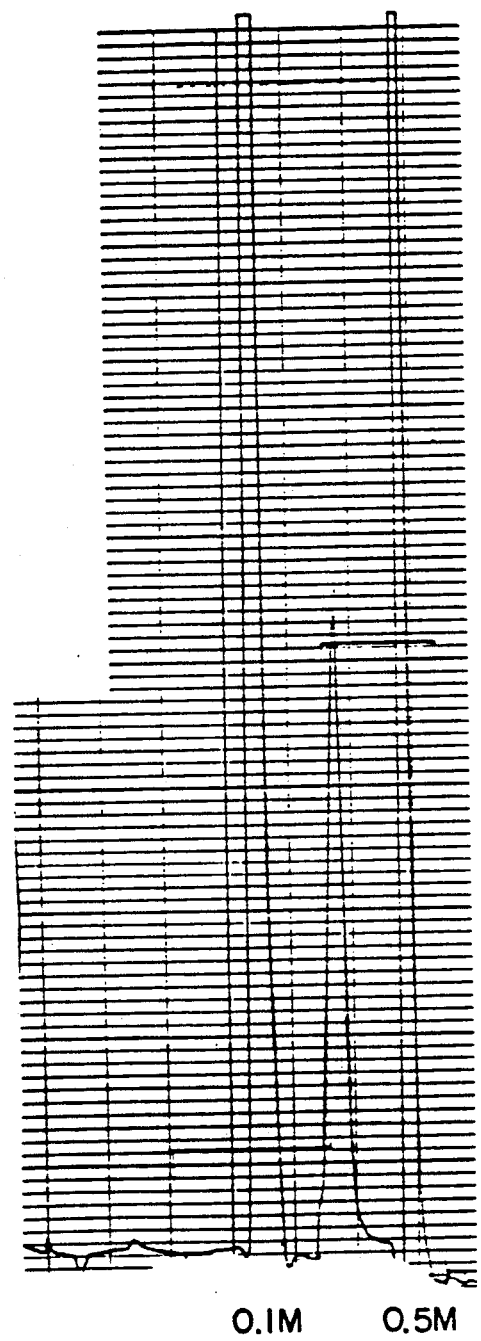
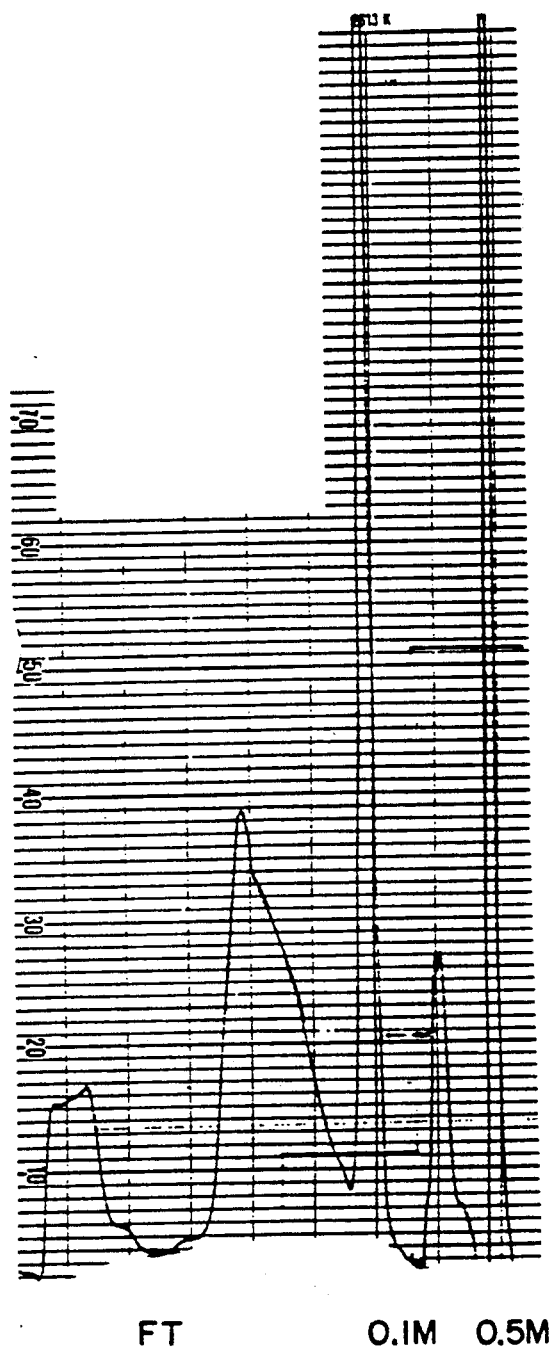

1 2 3 4 5 6

1 2 3 4 5 6 7 8

METHOD OF ENHANCING IMMUNOGLOBULIN FRAGMENT PRODUCTION

TECHNICAL FIELD

The present invention relates to methods of enhancing the yield of immunoglobulin fragments, such as Fab fragments, produced by fragmentation of immunoglobulins.

BACKGROUND OF THE INVENTION

The basic structural unit of an immunoglobulin features two light chains and two heavy chains. Each light chain is made up of a variable region and a constant region and is associated with a corresponding heavy chain. Each heavy chain is composed of a variable region and three constant regions, where the constant regions of the heavy chain are collectively longer than the constant region of the light chain and extend through a hinge region.

The Fab fragment of an immunoglobulin includes the entire light chain of the immunoglobulin and the variable region and a corresponding length of the constant region of the heavy chain. The lengths of both heavy chains extending beyond the Fab fragment and hinge region constitute the Fc fragment of the immunoglobulin. The F(ab')$_2$ fragment of an immunoglobulin includes both light chains and a length of both heavy chains, extending through the hinge region thereof and joined by disulfide bonds. Immunoglobulin fragments are useful in a number of therapeutic and diagnostic applications and exhibit greater utility than whole immunoglobulin for some of those purposes.

Fab and F(ab')$_2$ fragments are formed by proteolytic fragmentation reactions. Exemplary conventional fragmentation reactions are partial digestion with the proteolytic enzymes papain and pepsin. Papain treatment theoretically yields Fab fragment. Under some circumstances for some immunoglobulins, however, papain treatment results in low yields of Fab fragment. One method to increase the yield of Fab fragment is to conduct the fragmentation in the presence of cysteine. While the yield of Fab may be increased by this method, the quality of the Fab fragment produced may diminish, i.e., the Fab fragment produced may not be homogeneous. Pepsin treatment is used to produce F(ab')$_2$ fragment; however, problems exist in production of this fragment for certain immunoglobulins, where pepsin treatment results in the production of one Fab fragment and one Fab/Fc fragment.

Monoclonal antibodies are immunoglobulins as well as glycoproteins, i.e., proteins having sugar moieties covalently bound thereto through N and/or O glycosyl bonds. Carbohydrate moieties are generally bound to immunoglobulins at a location or locations in the Fc region. Carbohydrates may also be found at the hinge region or on the Fab portions of an immunoglobulin, however. Carbohydrate moieties located on immunoglobulins can contribute to the biological activity of the immunoglobulins in a number of ways, including the mediation of intracellular and intercellular immunoglobulin recognition.

The oligosaccharide units of glycoproteins may be varied and complex. The properties of these oligosaccharide units depend upon the composition of the sugar residues contained therein, including the anomeric configuration of each residue, the sequence of the sugar residues, the pattern of glycosidic linkages within the sequence, and the nature of the linkage of the oligosaccharide units to the protein.

Oligosaccharide moieties located on immunoglobulins are often capped with a terminal sialic acid moiety. As discussed in PCT Application No. US86/00495, published on Sept. 11, 1987, such immunoglobulins are not rapidly cleared from the bloodstream, because there appears to be no sialic acid specific receptor located on cells responsible for bloodstream clearance. In this PCT application, sialic acid residues are attached to a protein to be administered to a patient, thereby increasing the in vivo halflife and increasing the stability of that protein.

Desialylation reactions are used in U.S. Pat. No. 4,859,449 to expose underlying sugar residues in efforts to control the halflife of administered protein. Like the PCT Application described above, the methods, conjugates and kits of this patent are constructed in accordance with the notion that glycoproteins having exposed sugar residues recognized by certain receptors on cells active in blood clearance are cleared from the bloodstream more rapidly than glycoproteins having oligosaccharide units capped with sialic acid.

Although heavy chain Ig polypeptides encoded by a single constant region heavy chain gene typically migrate as a single molecular weight band ranging from about 52,000 to about 56,000 daltons under reduced conditions on SDS-polyacrylamide gel electrophoresis, double and triple heavy chain bands have been observed for murine immunoglobulins of the IgG$_{2b}$ and IgG$_{2a}$ isotypes (Kohler et al., 1978, *European J. Immunology*, 8: 82-88 and Leatherbarrow, R. J. et al., 1985, *Molecular Immunology* 22; 4, pp. 407-415). This observed heterogeneity in molecular weight of the heavy chains in these immunoglobulin isotypes has been attributed to differing glycosylation of the respective heavy chains.

SUMMARY OF THE INVENTION

The present invention provides methods of enhancing the yield of immunoglobulin fragments, such as Fab fragments, from fragmentarily intact immunoglobulins using conventional fragmentation reactions. The yield enhancement methods of the present invention include the steps of desialylating fragmentarily intact immunoglobulin; and fragmenting the immunoglobulin produced from the desialylation step. The fragmentation step of the method of the present invention may be conducted in the presence of cysteine, to provide an increase in fragment yield without decreasing the quality of the fragment produced.

Also discussed are methods of enhancing the molecular weight homogeneity of fragmentarily intact immunoglobulin or immunoglobulin fragments prepared in a conventional fragmentation reaction. These homogeneity enhancing methods include the steps of desialylating fragmentarily intact immunoglobulin or immunoglobulin fragment and purifying the desialylated product.

BRIEF DESCRIPTION OF THE DRAWINGS

FIG. 3 is an autoradiogram of an SDS-PAGE analysis conducted under reducing conditions of an IgG$_{2b}$ monoclonal antibody (metabolically labeled with $^{35}$S-methionine) demonstrating the conversion of the upper H band to the lower H band following neuraminidase treatment.

FIGS. 5A-5B show the results of a Mono Q Sepharose chromatographic separation of neuraminidase-treated and papain-digested NR-ML-05 monoclonal antibody, fragmented in the presence or absence of cysteine.

DESCRIPTION OF THE PPREFERRED EMBODIMENTS

For the purposes of this specification, the term "immunoglobulin" shall mean an Ig polypeptide, a monoclonal antibody, or the like. The immunoglobulin of the present invention may be an antibody of isotype IgG, IgM, IgA, IgE, or IgD. The immunoglobulin of the present invention may also be an Ig polypeptide derivative or other chemically modified Ig polypeptide.

An "immunoglobulin fragment" of the present invention is an immunoglobulin portion produced by conventional fragmentation reactions, such as a Fab fragment, or an immunoglobulin portion produced by other reactions or techniques. Specifically, an "immunoglobulin fragment" of the present invention is any immunoglobulin portion, exhibiting anomalous molecular weight indicating bands on SDS-PAGE or otherwise exhibiting molecular weight heterogeneity in a similar procedure.

A "fragmentarily intact immunoglobulin" of the present invention is an immunoglobulin that exhibits a fundamental unit of generally Y-shaped structure, including two light chains and two heavy chains. For example, a fragmentarily intact IgG immunoglobulin includes one generally Y-shaped fundamental unit, while a fragmentarily intact IgM immunoglobulin includes five generally Y-shaped fundamental units.

When disulfide bonds between the light and heavy chains of a fragmentarily intact immunoglobulin are broken, the immunoglobulin has been reduced. The fragmentarily intact immunoglobulin of the present invention exhibits anomalous bands when analyzed under reducing conditions by SDS-PAGE techniques or other technology indicating unexpected molecular weight differences in heavy or light immunoglobulin chains. A molecular weight difference in heavy chains is discussed below as exemplary.

Figure 1:
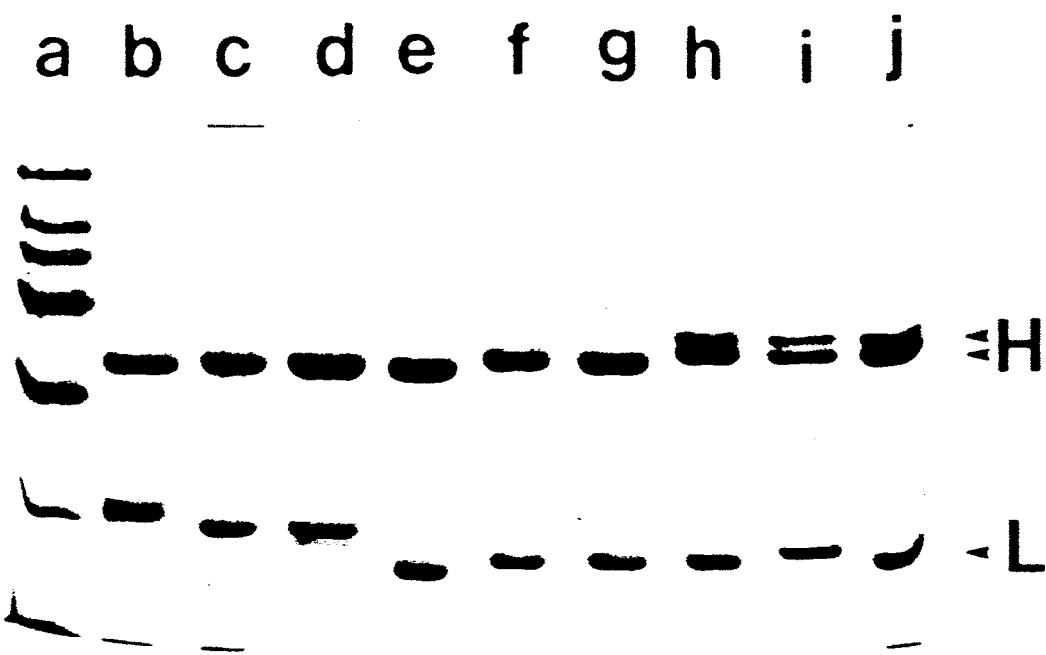
FIG. 1 shows the results of an SDS-PAGE analysis of purified, intact murine immunoglobulins of various isotypes under reducing conditions.

Analysis of a reduced fragmentarily intact IgG or other immunoglobulin isotype, for example, by SDS-PAGE techniques, typically results in a gel showing two bands, as shown in lanes b-g in FIG. 1. The lower molecular weight band is designated "L" in FIG. 1 and corresponds to the light immunoglobulin chain, while the higher molecular weight band is designated "H" in FIG. 1 and corresponds to the heavy immunoglobulin chain. Some fragmentarily intact immunoglobulins, such as IgG$_{2b}$ immunoglobulins, exhibit three bands when reduced and analyzed by SDS-PAGE techniques, as shown in lanes h-j of FIG. 1, i.e., one L band and two H bands. The higher molecular weight anomalous band indicates that two heavy chain polypeptides of differing molecular weights are present. For the purposes of this specification, these immunoglobulins exhibiting anomalous bands will be referred to as "doublet/triplet immunoglobulins."

Analysis of fragmentarily intact immunoglobulins by SDS-PAGE techniques under non-reducing conditions will not aid in identifying doublet/triplet immunoglobulins. Fragmentarily intact doublet/triplet immunoglobulins as well as other fragmentarily intact immunoglobulins resolve into a single band when analyzed on a non-reduced gel.

An alternative method of identifying doublet/triplet immunoglobulins involves analysis of the results of SDS-PAGE or other similar analyses of immunoglobulin fragments produced in fragmentation reactions conducted in the presence of cysteine. Purified Fab fragments of doublet/triplet immunoglobulins, for example, resolve into two bands (i.e., a doublet) on a non-reducing gel and three bands (i.e., a triplet) on a reducing gel, as shown, for example, in lane 4 of FIGS. 7 and 8, respectively. In contrast, purified immunoglobulin Fab fragments exhibiting heavy chain molecular weight homogeneity resolve into a single band on non-reducing gels and into a doublet on reducing gels. The immunoglobulin fragments of doublet/triplet immunoglobulins useful in the practice of the present invention therefore also exhibit an anomalous band.

Analysis of immunoglobulin fragments that were fragmented in the absence of cysteine by SDS-PAGE techniques will not aid in identifying doublet/triplet immunoglobulins, however. Doublet/triplet immunoglobulins that are fragmented in the absence of cysteine produce fragments that exhibit the same characteristics as fragmented immunoglobulins having heavy chain molecular weight homogeneity when analyzed by SDS-PAGE, i.e., resolve into a single band on a non-reducing gel and a doublet on a reducing gel, as shown in lane 3 in FIGS. 6 and 9, for example. As set forth above, murine IgG$_{2a}$ and IgG$_{2b}$ monoclonal antibodies, for example, have been demonstrated to exhibit anomalous bands. In fact, these anomalous band phenomena appear characteristic of IgG$_{2b}$ immunoglobulins.

Another method of identifying doublet/triplet immunoglobulins useful in the practice of the present invention involves observation of the proteolytic cleavage undergone by the immunoglobulin being tested. If the cleavage reaction is asymmetric with respect to the heavy chains, the immunoglobulin may be a doublet/triplet immunoglobulin. For example, pepsin cleavage typically results in F(ab')$_2$ immunoglobulin fragments. If, however, such cleavage results in Fab and Fab/Fc immunoglobulin fragments, asymmetric cleavage has occurred. Similarly, if papain digestion results in the formation of Fab and Fab/Fc immunoglobulin fragments, the immunoglobulin may be a doublet/triplet immunoglobulin.

Some immunoglobulins of the IgG$_{2b}$ and IgG$_{2a}$ subclasses have been demonstrated to exhibit asymmetric proteolytic cleavage as described above. See Parham, *J. Immunol.*, 131: 2895-2902, 1983 and Glennie and Stevenson, *Nature*, 295: 712-3, 1982.

Experiments involving IgG$_{2b}$ antibodies, for example, indicate that the anomalous band represents a heavy chain of differing molecular weight, rather than an immunoglobulin fragment cleaved at an alternative site or other anomalous fragment. The amino acid compositional analysis demonstrating this phenomena is discussed later in conjunction with achieving heavy chain molecular weight homogeneity.

Immunoglobulin fragment yield enhancing methods include the steps of desialylating fragmentarily intact doublet/triplet immunoglobulin; and thereafter fragmenting the desialylated immunoglobulin. This yield enhancement method exploits the observation that the differences in immunoglobulin heavy chain molecular weight are attributable to asymmetric sialylation of the heavy chains, rather than asymmetric glycosylation thereof.

Sialylation patterns vary across immunoglobulins. Specifically, different monoclonal antibodies will exhibit different sialylation patterns. Moreover, sialylation patterns may differ across various lots or batches of the same monoclonal antibody, depending on growth conditions, and the like.

Desialylation can be carried out in accordance with known techniques, as set forth in U.S. Pat. No. 4,859,449. One desialylating technique useful in the practice of the present invention is neuraminidase treatment as described below.

Neuraminidase Treatment of Monoclonal Antibodies

Murine immunoglobulins at a concentration of 1.9-2.5 mg/ml were treated with 3 U/ml of purified *clostridium perifringens* neuraminidase (Type X, Sigma, St. Louis, MO) for 48 hours at room temperature in 0.01M acetate buffer at pH 5.5, containing 1 mM PMSF protease inhibitor (Sigma, St. Louis, Mo.) and 0.02% thimerosal to prevent bacterial growth. Controls were incubated in the same buffer under identical conditions except without neuraminidase. Following the incubation period, both the neuraminidase-treated and control immunoglobulins were purified on separate Protein A-Sepharose CL-4B (Pharmacia, Piscataway, N.J.) columns as described by Ey et al., *Immunochemistry*, 15: 429-436, 1978.

Insoluble neuraminidase may also be used to achieve desialylation. Specifically, an intact doublet/triplet immunoglobulin or a fragment thereof may be incubated with neuraminidase covalently bound to aragose beads. This desialylation reaction would take longer to complete, but neuraminidase can be easily separated from the reaction mixture by removal of the neuraminidase-bound aragose beads. A practitioner in the art would be able to ascertain and employ appropriate neuraminidase binding and desialylation reaction conditions.

Figure 2:
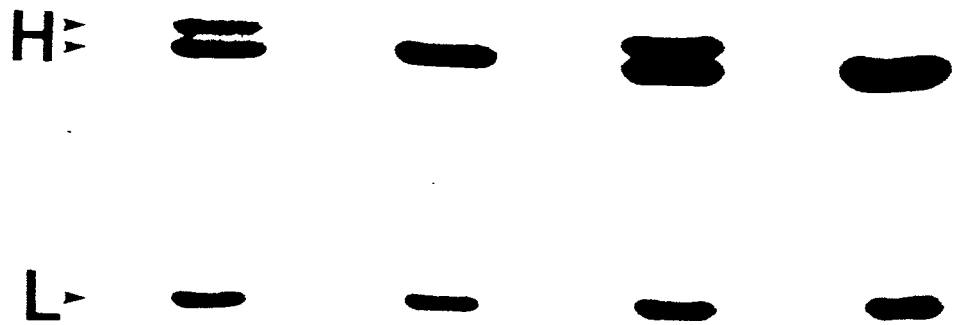
FIG. 2 shows the results of an SDS-PAGE analysis conducted under reducing conditions of intact IgG$_{2b}$ immunoglobulins purified following treatment with or without neuraminidase.
Figure 7:
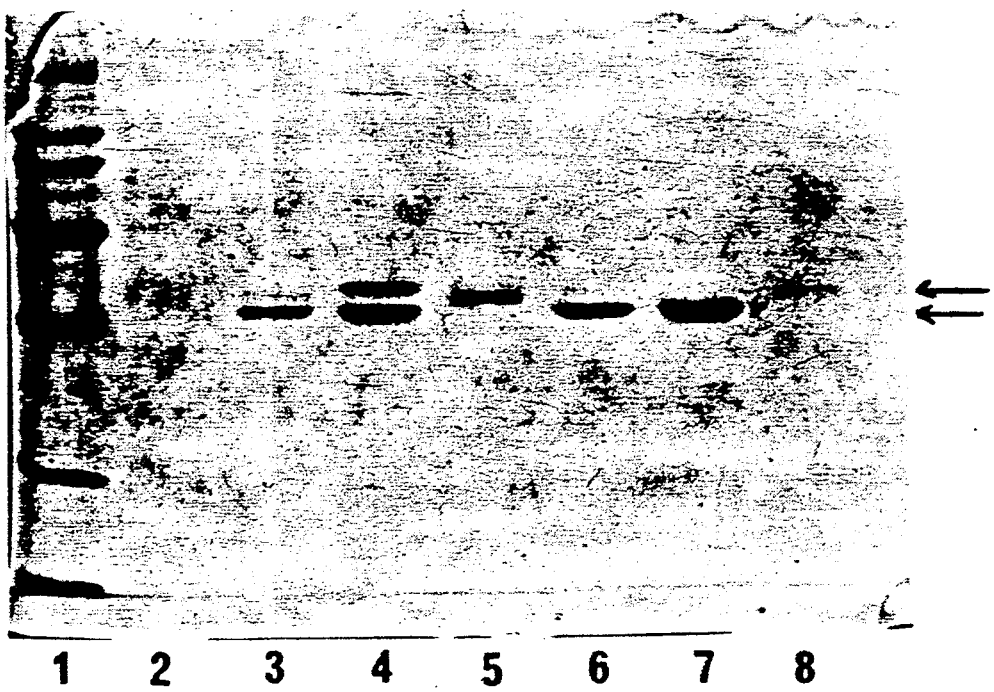
FIG. 7 shows the results of a 10% SDS-PAGE analysis conducted under non-reducing conditions of papain-digested NR-ML-05 monoclonal antibody, treated with or without neuraminidase and fragmented in the presence of cysteine and subsequently purified by Anion-Exchange Chromatography.

Once desialylation of intact immunoglobulin has taken place, both heavy chains of the immunoglobulin are of the same or substantially similar molecular weights as indicated by SDS-PAGE techniques performed on reduced immunoglobulin, i.e., the heavy chains of these immunoglobulins resolve into only a single band. This phenomena is shown in FIG. 2, where lanes 1 and 3 are IgG$_{2b}$ immunoglobulin controls and lanes 2 and 4 are neuraminidase-treated IgG$_{2b}$ immunoglobulins. When desialylation is followed by papain fragmentation conducted in the presence of cysteine, the purified Fab fragments resolve into a doublet on SDS-PAGE reduced gels and a single band on non-reduced gels. These phenomena are shown in FIG. 7, where lanes 4 and 7 are respectively 0.1M NaCl eluted control Fab fragments and Fab fragments derived from neuraminidase-treated immunoglobulin, and in FIG. 8, where lanes 4 and 5 are respectively 0.1M NaCl eluted control Fab fragments and 0.1M NaCl eluted Fab fragments derived from neuraminidase-treated immunoglobulin. In either case, the heavy chains of the desialylated glycoproteins are homogeneous in molecular weight.

Asymmetric glycosylation has also been hypothesized to result in the protection of one immunoglobulin heavy chain from proteolytic cleavage by papain or pepsin during conventional fragmentation reactions. See Parham, P., 1983, *S. Immunol.*, 131: 2895 and Glennie and Stevenson, 1982, *Nature*, 295: 712. Consequently, a Fab fragment and a Fab/Fc fragment are formed following fragmentation (papain or pepsin digestion). After desialylation of intact immunoglobulin, however, the desialylated immunoglobulin has heavy chains exhibiting the same or substantially similar molecular weight, and therefore both heavy chains and both light chains of the immunoglobulin will be exposed to the proteolytic enzyme affecting the fragmentation reaction to the same extent. As a result, the yield of the desired fragment is expected to increase. Consequently, immunoglobulin fragment yield enhancement may also be achieved by practicing the fragmentation step of the present invention in the absence of cysteine.

Another consequence of the desialylation/fragmentation method of the present invention is the homogeneity of the immunoglobulin fragments produced in the fragmentation reaction. This phenomena, indicated by the absence of anomalous bands on SDS-PAGE as described previously, may be the result of the exposure, through desialylation, of protease-sensitive sites that are normally conformationally protected by bound sialic acid residues. Homogeneity in product formation is essential to achieve purity levels required by the Food and Drug Administration for compositions to be administered to humans for therapeutic or diagnostic purposes. As a result, desialylation can be thought of as a homogeneity enhancing method.

Accordingly, the present invention also contemplates methods of enhancing the molecular weight homogeneity of fragmentarily intact double/triplet immunoglobulin or enhancing the homogeneity of the immunoglobulin fragments produced from fragmentation reactions involving doublet/triplet immunoglobulins. These homogeneity enhancing methods include the steps of desialylating fragmentarily intact doublet/triplet immunoglobulin or fragments thereof and purifying the desialylated immunoglobulin or immunoglobulin fragment.

The purification process of the present invention may be any process capable of separating the desialylated immunoglobulin or immunoglobulin fragment from the desialylation or fragmentation reaction product. An exemplary purification process is that employing protein A Sepharose columns described in Ey et al., *Immunochemistry*, 15: 429–436, 1978. Another purification method useful in the practice of the present invention is anion-exchange chromatography on Mono-Q columns available from Pharmacia LKB. A practitioner in the art could design and implement a purification process.

Also, the removal of terminal sialic acid moieties alters the charge characteristics of the fragmentarily intact immunoglobulin or immunoglobulin fragment. Consequently, different charge-utilizing purification techniques may be used with the desialylated moieties produced in the methods of the present invention than are used with the sialylated counterparts thereof. Again, a practitioner in the art could design and implement such a purification process.

The fragmenting step of the method of the present invention may be any method sufficient to produce immunoglobulin fragments, such as Fab, F(ab')$_2$, and the like. Conventional fragmentation reactions, such as partial digestion with papain or pepsin, may be employed for this purpose. Exemplary immunoglobulin fragmenting protocols are set forth in Harlow and Lane, "Antibodies A Laboratory Manual", Cold Spring Harbor Laboratory, pp. 628–631, 1988 and the "Handbook of Experimental Immunology Volume 1 Immunochemistry." pp. 14.1–14.23, 1986.

An additional advantage of the present invention is that doublet/triplet immunoglobulins may be fragmented in the presence of cysteine to obtain an increase in immunoglobulin fragment yield without a decrease in the quality of that yield. Table I includes experimental results demonstrating this increased yield.

As stated previously, doublet/triplet immunoglobulins useful in the present invention behave as homogeneous immunoglobulins when fragmented in the absence of cysteine. Cysteine has been added to fragmentation reaction mixtures to increase fragment yield, probably through exposure of protease-sensitive sites resulting from reduction of disulfide bands in the immunoglobulin hinge region. For doublet/triplet immunoglobulins, however, the presence of cysteine in the fragmentation reaction mixture results in heterogeneity of the fragments produced in that reaction.

When desialylation is undertaken prior to fragmentation conducted in the presence of cysteine, however, the fragmentation reaction product is homogeneous in molecular weight. Specifically, no anomalous bands were observed in post-fragmentation analysis of the reaction product by SDS-PAGE techniques, as shown, for example, in lane 7 of FIG. 7 and FIG. 9, lane 4.

Experimentation was conducted to demonstrate the phenomena described above. The monoclonal antibodies or the cell lines that secreted monoclonal antibodies used in those experiments, which are detailed below, were as follows. NR-Lu-11 (IgG$_1$, k) and NR-Lu-10 (IgG$_{2b}$, k) were prepared in house. DB1-44 (IgG$_1$, k) are obtainable in accordance with Colcher et al., *Proc. Natl. Acad. Sci. (U.S.A.)*, 78: 3199, 1981. 9.2.27 (IgG$_{2a}$, k) are obtainable in accordance with Morgan et al., *Hybridoma*, 1: 27, 1981. NR-2AD (IgG$_{1a}$, k) are obtainable in accordance with Thielmans et al., *J. Immunol.*, 133: 495, 1984. NR-Co-01 (IgG$_3$, k) and NR-Co-04 (IgG$_3$, k) were generated as described by Woodhouse et al., *Cancer Research*, 49: 2766, 1989. NR-M1-05 (IgG2b, k) are obtainable in accordance with Woodhouse et al., "In Human Melanoma. From Basic Research to Clinical Application," Ferrone, ed., Springer-Verlag, pp. 151–163, 1990. OVB-3 (IgG$_{2b}$, k) are obtainable in accordance with Fitzgerald et al., *Proc. Natl. Acad. Sci. (U.S.A.)*, 83: 6627, 1986.

Immunoglobulins used in the following experiments were purified from culture supernatant by ammonium sulfate precipitation and anion-exchange chromatography and judged to be greater than 95% pure by SDS-PAGE as determined by densitometric scanning.

Analyses of Fragmentarily Intact Immunoglobulins.

Sodium dodecyl sulfate polyacrylamide gel electrophoresis (SDS-PAGE) of purified immunoglobulins was performed under reducing conditions in 10% separation gels according to the method of Laemmli, *Nature*, 227: 680–5, 1970. Molecular weights of heavy chains and light chains were determined from molecular weight standards (BioRad, Richmond, Calif.) run simultaneously.

The results of SDS-PAGE studies on purified, fragmentarily intact immunoglobulins conducted under reducing conditions are shown in FIG. 1, with lane a corresponding to the standard molecular weight markers; lanes b and e corresponding to IgG$_1$ isotype immunoglobulins; lanes c and d corresponding to IgG$_{2a}$ isotype immunoglobulins; lanes f and g corresponding to IgG$_3$ isotype immunoglobulins; and lanes h-j corresponding to IgG$_{2b}$ isotype immunoglobulins. The molecular weight of each band increases from the bottom to the top of FIG. 1. As a result, the band(s) located closer to the top of FIG. 1 and designated H are of higher molecular weight than those located below and designated L. On a reducing gel, typical fragmentarily intact immunoglobulins resolve into two bands, one H band and one L band. In these experiments, only the IgG$_{2b}$ immunoglobulin subclass exhibited a band indicating the presence of an anomalous, second heavy chain.

Consequently, these immunoglobulins were identified as doublet/triplet immunoglobulins.

Neuraminidase Treatment of Monoclonal Antibodies

Murine immunoglobulins at a concentration of 1.9–2.5 mg/ml were treated with 3 U/ml of purified clostridium perifringens neuraminidase (Type X, Sigma, St. Louis, Mo.) for 48 hours at room temperature in 0.01M acetate buffer at pH 5.5, containing 1 mM PMSF protease inhibitor (Sigma, St. Louis, Mo.) and 0.02% thimerosal to prevent bacterial growth. Controls were incubated in the same buffer under identical conditions except without neuraminidase. Following the incubation period, both the neuraminidase-treated and control immunoglobulins were purified on separate Protein A-Sepharose CL-4B (Pharmacia, Piscataway, N.J.) columns as described by Ey et al., *Immunochemistry*, 15: 429–436, 1978.

SDS-PAGE analysis of the desialylated immunoglobulins was conducted as described above. As shown in FIG. 2, neuraminidase treatment resulted in the resolution of the two heavy chain bands into a single molecular weight band of approximately 53,000 daltons.

In order to demonstrate that the lower heavy chain band was derived from the upper heavy chain band, doublet/triplet immunoglobulin was metabolically-labeled with $^{35}$S-methionine in accordance with the following procedure. IgG$_{2b}$ -secreting hybridoma cells ($2 \times 10^7$) were incubated in 5 ml of methionine-free RPMI-1640 (Whittaker M.A. Bioproducts, Walkersville, Md.) for 1 hour to deplete the amino acid pool of methionine. This was followed by incubation at 37° C. in 5.5 ml of methionine-free RPMI-1640 containing dialyzed fetal calf serum and 100 uCi/ml of $^{35}$S-methionine (Tran$^{35}$S-label, ICN, Irvine, Calif.) for 0.5 hours. Cells were then washed free of the $^{35}$S-methionine-containing media, resuspended in RPMI containing 10X concentration of cold methionine and incubated at 37° C. for 4 hours. Following incubation, cells were separated from media by centrifugation at 1200×g for 5 minutes. Labeled immunoglobulin was purified from the conditioned media by adsorption onto Protein A Sephrarose CL-4B essentially as described by Ey et al., *Immunochemistry*, 15: 429-436, 1978. Purified immunoglobulin was analyzed by SDS-PAGE according to the method described by Laemmli, *Nature*, 227: 680-5, 1970.

Treatment of purified metabolically-labeled immunoglobulin with neuraminidase resulted in disappearance of the upper heavy chain band accompanied by an increase of activity in the lower molecular weight heavy chain band, as shown in FIG. 3, lane 2. This result demonstrated that the polypeptide component of the upper band was common to the lower band and that the difference in molecular weight was most likely a result of sialylation.

This hypothesis was further supported by amino acid compositional analysis. Purified non-desialylated and desialylated IgG$_{2b}$ immunoglobulins were subjected to vapor phase hydrolysis using constant boiling 6N HCl in an inert atmosphere for 55 minutes at 160° C. To minimize loss of unstable residues, β-mercaptoethanol and phenol were added. Hydrolyzates were analyzed by ion-exchange HPLC using post-column ninhydrin reaction on a Beckman Model 6300 Amino Acid Analyzer. Amino acid composition was presented as mole % composition. The mean values for each residue were essentially the same for both samples. These results demonstrate that heavy chain molecular weight heterogeneity was not due to proteolysis.

In addition, this finding of commonality in heavy chain structure following desialylation is consistent with the more acidic properties exhibited by the heavy chain of higher molecular weight when compared with the heavy chain of lower molecular weight. This observation was the result of isoelectric focusing work described in Kohler et al., *European J. Immunol.*, 8: 82-88, 1978.

Immunoreactivity of Fab Fragments.

The immunoreactivity of purified NR-ML-05 Fab produced from desialylated and non-desialylated NR-ML-05 immunoglobulin was determined by competitive inhibition ELISA using biotinylated intact NR-ML-05 (Engvall et al., *Immunochemistry*, 8: 871, 1971). Polyvinyl microtiter wells were coated with extracts of A375 M/M cells (American Type Culture Collection, Rockville, Md.) solubilized with 0.1% NP-40 detergent. Dilutions of purified Fab from desialylated or non-desialylated NR-ML-05 were mixed with a fixed amount of biotinylated NR-ML-05 antibody and added to extract-coated wells. Following incubation for 1 hour at 25° C., the wells were washed free of unbound antibody. Bound biotinylated NR-ML-05 was detected with horseradish peroxidase-conjugated streptavidin and 2,2'-azinobis(3-ethylbenzthiazoline sulfonic acid). Fab fragments produced from desialylated NR-ML-05 were unaffected in immunoreactivity, exhibiting similar properties to control Fab.

Analyses of Immunoglobulin Fragments.

NR-ML-05 IgG$_{2b}$ immunoglobulin was treated with neuraminidase and purified by adsorption onto protein A Sepharose as described above. Control NR-ML-05 was treated in the same manner without neuraminidase. Purified immunoglobulin was fragmented in both the absence and presence of cysteine using papain. 250 μg of antibody was digested at a concentration of 1.25 mg/ml. Papain (250 μl, Pierce Corp.) was activated for 1 hour at 37° C. in 10 mM EDTA and 20 mM cysteine. Activated papain was added at 250 ml/8 mg antibody, and the reaction mixture was incubated for 18 hours at 37° C. end over end in the presence or absence of 20 mM cysteine.

Figure 4A:
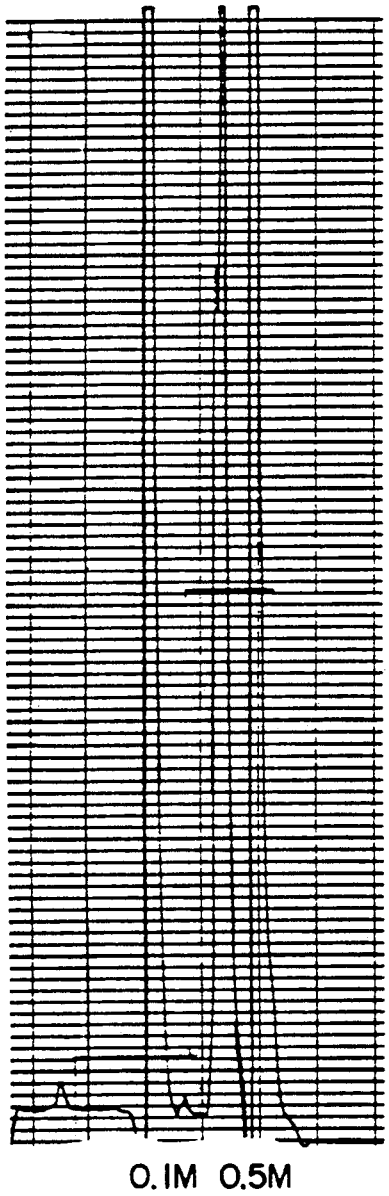
FIGS. 4A-4B show the results of Mono Q Sepharose chromatographic separation of papain-digested NR-ML-05 monoclonal antibody, fragmented in the presence or absence of cysteine.
Figure 4B:
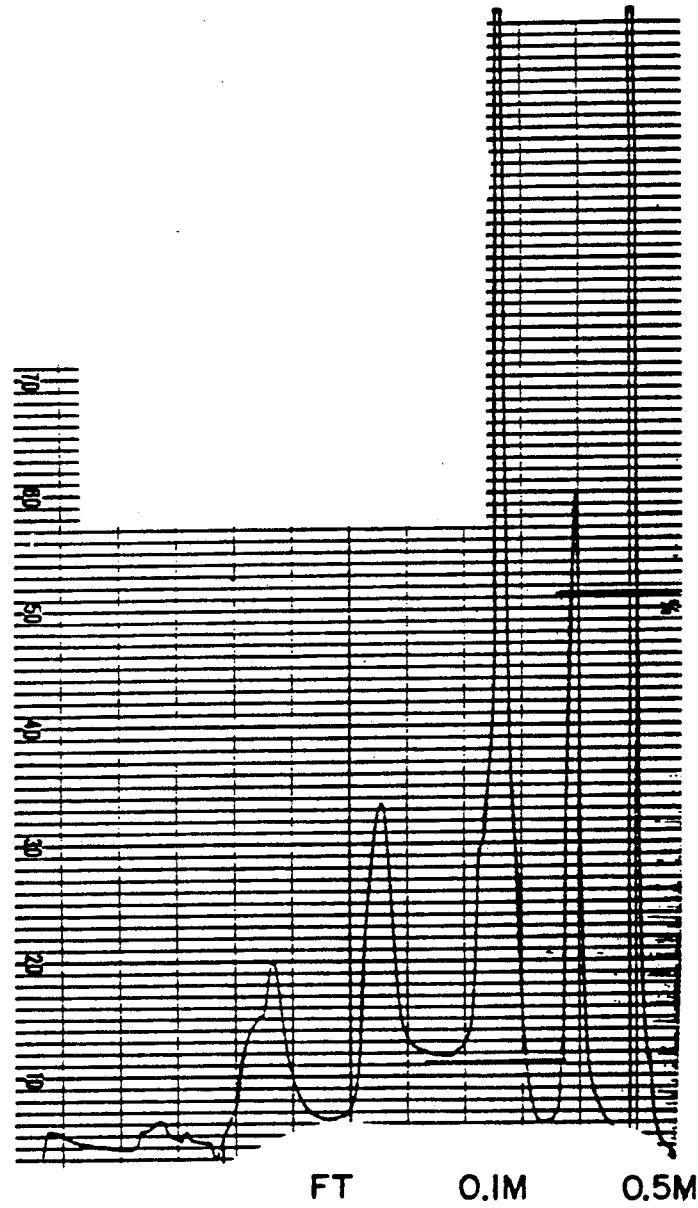

Products of the fragmentation reaction were purified by anion-exchange chromatography on Mono Q (Pharmacia LKB) as shown in FIGS. 4 and 5. The sample was applied to the ion-exchange column in 0.005M phosphate at pH 8.0. The column flow through was collected, and fragments were eluted with NaCl. FIGS. 4 and 5 show elution profiles of papain digest flow through, 0.1M NaCl eluate, and 0.5M NaCl eluate. Undigested IgG appears in the flow through. Fab fragments are eluted in the 0.1M NaCl peak. The 0.5M NaCl eluate contains Fc and other immunoglobulin fragments. Fab fragment purified by elution in 0.1M NaCl was analyzed by both reducing and non-reducing SDS-PAGE.

Figure 6:
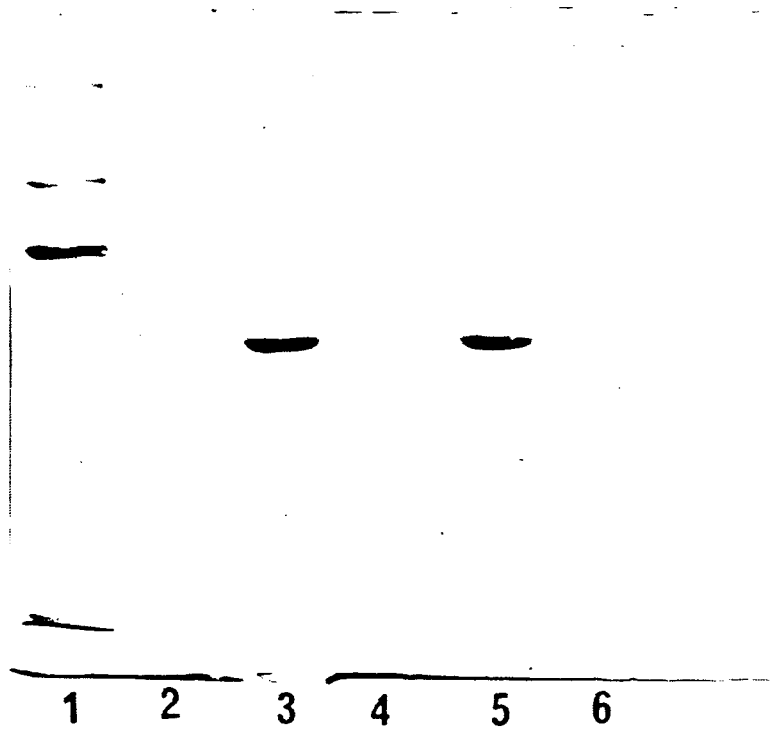
FIG. 6 shows the results of a 10% SDS-PAGE analysis conducted under non-reducing conditions of papain-digested NR-ML-05 monoclonal antibody, treated with or without neuraminidase and fragmented in the absence of cysteine and subsequently purified by Anion-Exchange Chromatography.

Purified Fab fragment produced by fragmenting non-desialylated immunoglobulin in the absence of cysteine migrated as a single molecular weight band on non-reduced gels, as shown in FIG. 6, lane 3. Fab fragment produced from the same immunoglobulin by fragmentation in presence of cysteine migrated as two molecular weight species on a non-reduced gel (FIG. 7, lane 4).

Although no difference was observed on reducing gel SDS-PAGE in the Fab fragment generated from non-desialylated and desialylated immunoglobulins in the absence of cysteine (compare lanes 3 and 5 in FIG. 6), a clear difference was observed when the fragmentation was conducted in the presence of cysteine (compare lanes 4 and 7 in FIG. 7). Fab fragment produced from neuraminidase-treated immunoglobulin analyzed on a non-reduced gel migrated as a single band (FIG. 7, lane 7) while Fab produced from non-neuraminidase-treated immunoglobulin migrated as two bands (FIG. 7, lane 4).

Figure 8:
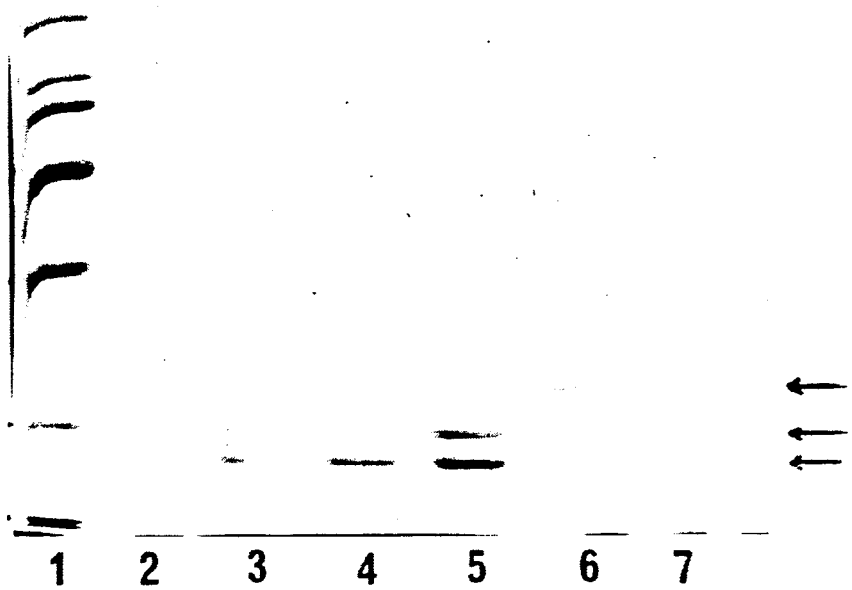
FIG. 8 shows the results of a 10% SDS-PAGE analysis conducted under reducing conditions of papain-digested NR-ML-05 monoclonal antibody, treated with or without neuraminidase and fragmented in the presence of cysteine and subsequently purified by Anion-Exchange Chromatography.

When analyzed under reducing SDS-PAGE, cysteine-generated Fab fragment from non-neuraminidase treated immunoglobulins migrated as three molecular weight species (FIG. 8, lane 4). Cysteine-generated Fab fragment from neuraminidase-treated immunoglobulins migrated as two molecular weight species, a heavy chain and a light chain (FIG. 8, lane 5).

Figure 9:
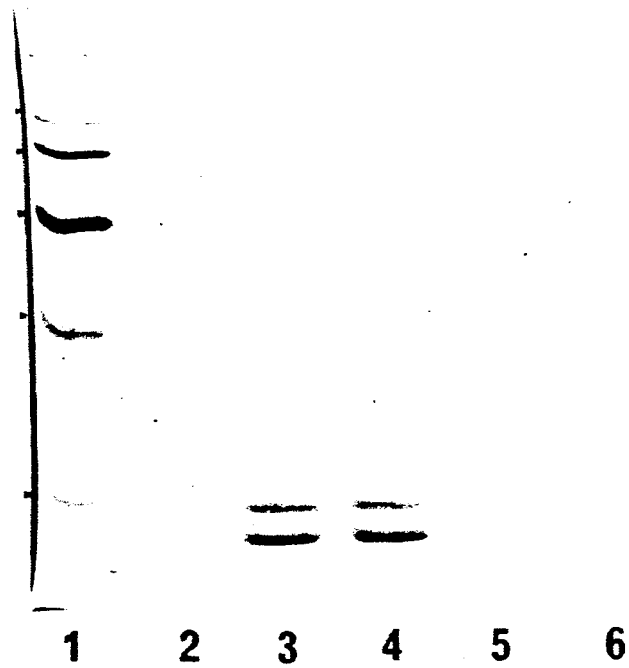
FIG. 9 shows the results of a 10% SDS-PAGE analysis conducted under reducing conditions of papain-digested NR-ML-05 monoclonal antibody, treated with or without neuraminidase and fragmented in the absence of cysteine and subsequently purified by Anion-Exchange Chromatography.

No difference was observed for Fab fragments generated in the absence of cysteine from neuraminidase-treated or non-neuraminidase-treated immunoglobulins under reducing as well as non-reducing SDS-PAGE conditions (FIG. 6, lanes 3 and 5 in addition to FIG. 9, lanes 3 and 4).

Enhanced Immunoglobulin Fragment Yield

Equal quantities of neuraminidase treated and non-neuraminidase treated NR-M1-05 immunoglobulins were fragmented in the presence of cysteine using papain and purified by anion-exchange chromatography as described above. Protein quantities were determined by BCA assay (Pierce Corp.). Smith, et al., *Anal. Biochem.*, 150, 76-85, 1985 describes a BCA protein assay procedure. In addition, a microtiter BCA assay procedure is described in Redinbaugh et al., *Anal. Biochem.*, 153: 267-71, 1986. The results of this quantitative testing are set forth in Table I below.

TABLE I

| Treatment | Fab Yield* ($\mu$g) | Percent Fab |
|---|---|---|
| None | 8 | 3.2 |
| Neuraminidase | 14 | 5.6 |

*Average of duplicate protein determination by BCA Assay.

These fragmentation experimental results demonstrate that fragmentation of neuraminidase-treated doublet/triplet immunoglobulins in the presence of cysteine generates a homogeneous preparation of Fab fragments at higher yield. In fact, Table I indicates the achievement of an almost two-fold increase in the yield of Fab fragment was achieved using the method of the present invention.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

We claim:

1. A method of yield enhancement of an immunoglobulin fragment comprising:
   (a) desialylating doublet/triplet immunoglobulin; and
   (b) fragmenting the immunoglobulin produced in step (a).

2. A method of yield enhancement according to claim 1 wherein the fragmenting step is conducted in the presence of an amount of cysteine effective to enhance immunoglobulin fragment yield.

3. A method of yield enhancement according to claim 1 wherein the immunoglobulin fragment is an F(ab')$_2$ fragment.

4. A method of yield enhancement according to claim 2 wherein the immunoglobulin fragment is an Fab fragment.

5. A method of yield enhancement according to claim 2 wherein the immunoglobulin is an Ig glycoprotein.

6. A method of yield enhancement according to claim 2 wherein the immunoglobulin is an IgG monoclonal antibody.

7. A method of yield enhancement according to claim 2 wherein the immunoglobulin is a murine IgG$_{2b}$ monoclonal antibody.

8. A method of yield enhancement according to claim 2 wherein the desialylating agent which is used comprises neuraminidase.

* * * * *